US00PP10377P

United States Patent [19]

Tanaka et al.

[11] Patent Number: Plant 10,377

[45] Date of Patent: May 5, 1998

[54] FUCHSIA PLANT, SANISTANF

[75] Inventors: Toshi Tanaka, Ashiya; Hidefumi Funakoshi, Takarazuka; Kenkichi Nose, Ashiya; Ushio Sakazaki, Hikone, all of Japan

[73] Assignees: Suntory Limited, Osaka; Nishinomiya City, Hyogo, both of Japan

[21] Appl. No.: 788,460

[22] Filed: Jan. 28, 1997

[51] Int. Cl.[6] ..... A01H 5/00

[52] U.S. Cl. ..... Plt./84

[58] Field of Search ..... Plt./84

*Primary Examiner*—James R. Feyrer

*Attorney, Agent, or Firm*—Burns, Doane, Swecker & Mathis, L.L.P.

[57] ABSTRACT

Disclosed herein is a fuchsia plant, having a spreading growth habit of strongly bushy form and which has thick stems. The brace roots and stems of the fuchsia plant are thick and strong, and so it needs no support. The fuchsia plant has great profusion blooms, the whole bush remaining in bloom for a considerable period of time, and very long flowering duration. The flowers are single and not having variegated pattern on petals, the petals having a deep violet to moderate purple color, and having vivid red sepals without variegated pattern and vivid red calyx tube without variegated pattern. The plant has a high resistance to heat, cold and disease, and medium resistance to pest, and it is able to growing in outdoor garden during the term of intense summer heat.

2 Drawing Sheets

BACKGROUND OF THE VARIETY

The present invention relates to a new and distinct variety of fuchsia plant obtained from the crossing of one fuchsia plant "FR19" (♂) native to Brazil and the other fuchsia plant "Fuchsia hybrida 1" (♀).

The fuchsia plant is a very popular plant in the United States and Europe and is used for potting in the spring season to summer season. But the fuchsia plant have a weak resistance to heat and it is necessary to grow them in air-conditioned rooms during the term of intensity of heat. Especially in Japanese summer, the heat is intense and it is necessary that the fuchsia plants grow in air-conditioned room, so the fuchsia plant were not become popular. Accordingly, this invention was aimed at obtaining a new variety having a strong resistance to heat and spreading growth habit.

The new variety of fuchsia plant according to this invention originated from crossing one fuchsia plant called "FR19" (♂) native to Brazil and the other fuchsia plant "Fuchsia hybrida 1" (♀).

First of all, one wild type of fuchsia plant called "FR19" was selected from 190 fuchsia plant varieties native to Brazil which the seeds introduced to Japan in February, 1991. And then 500 seedlings were obtained from crossing the wild type of fuchsia plant called "FR19" native to Brazil as pollen parent and the other fuchsia plant "Fuchsia hybrida 1" as female parent in the spring, 1992. From this crossing, 119 seedlings were selected in view of heat resistance and growth habit and then 19 seedlings was selected heat residence test in outdoors garden in 1993. These 19 seedling were grown and carried out a trial by flower potting in open-air field from the spring of 1994. The summer of 1994 is abnormal weather and intense then usual, and then the one plant which could be grown in open-air field and gained excellent result of apical meristem culture test selected in Autumn, 1994. The botanically characteristics of the finally-selected one plant were examined, using similar variety "Fuchsia hybrida 1" and "Fuchsia hybrida 2" for comparison, from the spring of 1994. As a result, it was concluded that this fuchsia is distinguishable from any other variety, whose existence is known to us, sufficiently uniform and stable in its characteristics, then this new variety of fuchsia plant was named "SANISTANF".

In the following description , the color-coding is in accordance with the Horticultural Colour Chart of The Royal Horticultural Society, London, England (R.H.S. Colour Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The pollen parent use in the crossing of "SANISTANF" was a wild type of fuchisa plant called "FR19" native to Brazil, the seeds introduced to Japan in February, 1991. The fuchsia plant "FR19" having a spreading growth habit, bright red colored sepal, single flowers, deep violet colored petal, and a high resistance to heat.

The female parent use in the crossing of "SANISTANF" was "Fuchsia hybrida 1". "Fuchsia hybrida 1" was a garden variety and was bought in a shop in the spring of 1992 in Hyogo-ken, Japan.

The wild type of fucshia plants "FR19" and the garden variety "Fuchsia hybrida 1" are presently maintained at the Plant Biotechnology Laboratory of SUNTORY Ltd., residing at 863-1, Aza-Iketani, Oomori-cho, Youkaichi-shi, Shiga-ken, Japan and at the Plant Research Center of NISHINOMIYA-SHI, residing at 1-1, Kitayama-cho, Nishinomiya-shi, Hyogo-ken, Japan.

"Fuchsia hybrida 1" which is the female parent of "SANISTANF" used for examination as a comparison are as follows.

Plant:

*Growth habit.*—Spreading.

*Plant height.*—Medium.

*Grade of bushiness.*—Medium.

Stem:

*Thickness.*—2.4 mm.

*Color.*—Red.

*Pubescence.*—Normal.

*Branching.*—Medium.

*Length of internode.*—Medium.

Leaf:
*Phyllotaxis.*—Opposite.
*Shape.*—Ovate.
*Tip form of leaf.*—Acute.
*Base form of leaf.*—Orbicular.
*Shape of margin.*—Dentate serrate.
*Length.*—44.5 mm.
*Width.*—23.4 mm.
*Thickness.*—0.3 mm.
*Color of upper surface of new leaf.*—Dark olive green. (R.H.S. 139A, J.H.S. 3707).
*Color of upper surface of mature leaf.*—Dark yellowish green. (R.H.S. 139A, J.H.S. 4007).
*Color of under surface of mature leaf.*—Moderate yellow green (R.H.S. 146B, J.H.S. 3514) with deep red (R.H.S. 60A, J.H.S. 0108) dots.
*Variegation on upper surface.*—Absent.
*Color of leaf vein.*—Purplish red.
*Luster.*—Absent.
*Pubescence of upper surface.*—Few.
*Pubescence of under surface.*—Few.
*Length of petiole.*—17.0 mm.
*Width of petiole.*—1.5 mm.
*Color of petiole.*—Deep red. (R.H.S. 60A, J.H.S. 0108).
*Pubescence of petiole.*—Medium.

Flower:
*Inflorescence types.*—Leaf axil — single.
*Facing direction.*—Downward to horizontal.
*Type.*—Single.
*Diameter.*—37.6 mm.
*Length.*—29.1 mm.
*Diameter of corolla.*—Medium.
*Shape of petal.*—Obovate.
*Length of petal.*—18.1 mm.
*Width of petal.*—17.9 mm.
*Thickness of petal.*—0.3 mm.
*Number of petals.*—Medium;4.
*Color of petal at the beginning of blooming time.*—Pinkish white. (R.H.S. 49C, J.H.S. 0101).
*Color of petal at blooming time.*—Pinkish white. (R.H.S. 49C, J.H.S. 0101).
*Variegated pattern of petal.*—Present; vein pattern.
*Color of variegated pattern of petal.*—Vivid red. (R.H.S. 57A, J.H.S. 0107).
*Shape of sepal.*—Oblong.
*Tip form of sepal.*—Acute.
*Calyx rolling.*—Medium (half up).
*Intorsion of sepal.*—Medium.
*Curvature of sepal.*—Flat.
*Length of sepal.*—30.5 mm.
*Width of sepal.*—7.9 mm.
*Thickness of sepal.*—0.5 mm.
*Number of sepals.*—Medium; 4.
*Color of sepal.*—Deep pink. (R.H.S. 51A, J.H.S. 0113).
*Variegated pattern on sepal.*—Present; vein pattern.
*Color of variegated pattern of sepal.*—Deep pink. (R.H.S. 51A, J.H.S. 0113).
*Shape of calyx tube.*—Long-tubular.
*Thickness of calyx tube.*—4.4 mm.
*Length of calyx tube.*—9.0 mm.
*Color of calyx tube.*—Deep pink. (R.H.S. 51A, J.H.S. 0113).
*Variegated pattern on calyx tube.*—Present; vein pattern.
*Color of variegated pattern of calyx tube.*—Vivid red. (R.H.S. 57A, J.H.S. 0107).
*Length of pistil.*—Long.
*Color of pistil.*—Strong purplish pink. (R.H.S. 55A, J.H.S. 9705).
*Color of stigma.*—Strong purplish pink. (R.H.S. 55A, J.H.S. 9705).
*Length of stamen.*—Medium.
*Color of stamen.*—Strong purplish pink. (R.H.S. 55A, J.H.S. 9705).
*Number of stamens.*—Medium; 8.
*Thickness of peduncle.*—Medium.
*Length of peduncle.*—Medium.
*Color of peduncle.*—Vivid yellow green. (R.H.S. 140A, J.H.S. 3105).
*Shape of ovary.*—Elliptic.
*Length of ovary.*—Short.
*Color of ovary.*—Strong yellow green. (R.H.S. 143A, J.H.S. 3711).
*Number of flowers.*—Medium.
*Flower fragrance.*—Absent.
*Floriferousness.*—Few.
*Grade of seed fertility.*—Medium.
*Grade of floral abscission.*—Easy.
*Blooming time.*—Early.
*Flowering duration.*—Short; May to June and September to October.

Physiological and ecological characteristics:
*Grade of cold resistance.*—Medium.
*Grade of heat resistance.*—Medium.
*Grade of disease resistance.*—Strong.
*Grade of pest resistance.*—Medium.

"Fuchsia hybrida 2" was used for examination as a comparison are as follows.

Plant:
*Growth habit.*—Spread.
*Plant height.*—Medium.
*Grade of bushiness.*—Few stems.

Stem:
*Thickness.*—1.7 mm.
*Color.*—Purplish red.
*Pubescence.*—Few.
*Branching.*—Medium.
*Length of internode.*—Short.

Leaf:
*Phyllotaxis.*—Opposite.
*Shape.*—Elliptic.
*Tip form of leaf.*—Acute.
*Base form of leaf.*—Orbicular.
*Shape of magrin.*—Dentate serrate.
*Length.*—38.6 mm.
*Width.*—24.4 mm.
*Thickness.*—0.3 mm.
*Color of upper surface of new leaf.*—Moderate olive green. (R.H.S. 146A, J.H.S. 3508).
*Color of upper surface of mature leaf.*—Dark olive green. (R.H.S. 132A, J.H.S. 3708).
*Color of under surface of mature leaf.*—Strong yellow green. (R.H.S. 143A, J.H.S. 3711).
*Variegation on upper surface.*—Absent.
*Color of leaf vein.*—Pale green.
*Luster.*—Weak.
*Pubescence of upper surface.*—Few.
*Pubescence of under surface.*—Few.

*Length of petiole.*—15.4 mm.
*Width of petiole.*—1.4 mm.
*Color of petiole.*—Moderate red. (R.H.S. 184B, J.H.S. 0115).
*Pubescence of petiole.*—Few.

Flower:
*Inflorescence types.*—Leaf axil — single.
*Facing direction.*—Downward to horizontal.
*Type.*—Double.
*Diameter.*—39.9 mm.
*Length.*—29.8 mm.
*Diameter of corolla.*—Medium.
*Shape of petal.*—Obovate.
*Length of petal.*—13.7 mm.
*Width of petal.*—13.5 mm.
*Thickness of petal.*—0.3 mm.
*Number of petals.*—Numerous; over 8.
*Color of petal at the beginning of blooming time.*—Deep purple; (R.H.S. 86A, J.H.S. 8307).
*Color of petal at blooming time.*—Deep purple. (R.H.S. 86A, J.H.S. 8307).
*Variegated pattern of petal.*—Present; primary pattern is splashed pattern, secondary pattern is vein pattern.
*Color of variegated pattern of petal.*—Color of primary pattern is purple, color of secondary pattern is red.
*Shape of sepal.*—Ovate.
*Tip form of sepal.*—Acuminate.
*Calyx rolling.*—None (full down).
*Intorsion of sepal.*—None.
*Curvature of sepal.*—Incurve.
*Length of sepal.*—18.3 mm.
*Width of sepal.*—11.2 mm.
*Thickness of sepal.*—0.5 mm.
*Number of sepals.*—Medium; 4.
*Color of sepal.*—Strong red.
*Variegated pattern on sepal.*—Absent.
*Shape of calyx tube.*—Long-tubular.
*Thickness of calyx tube.*—4.8 mm.
*Length of calyx tube.*—12.0 mm.
*Color of calyx tube.*—Strong purplish red. (R.H.S. 57D, J.H.S. 9706).
*Variegated pattern on calyx tube.*—Absent.
*Length of pistil.*—Medium.
*Color of pistil.*—Vivid red. (R.H.S. 52A, J.H.S. 0106).
*Color of stigma.*—Deep purplish pink. (R.H.S. 55A, J.H.S. 9705).
*Length of stamen.*—Medium.
*Color of stamen.*—Vivid red. (R.H.S. 57A, J.H.S. 0107).
*Number of stamens.*—Medium; 8.
*Thickness of peduncle.*—Medium.
*Length of peduncle.*—Medium.
*Color of peduncle.*—Moderate red. (R.H.S. 181B, J.H.S. 0416).
*Shape of ovary.*—Oblong.
*Length of ovary.*—Medium.
*Color of ovary.*—Strong yellow green, (R.H.S. 144A, J.H.S. 3507).
*Number of flowers.*—Few.
*Flower fragrance.*—Absent.
*Floriferousness.*—Medium.
*Grade of seed fertility.*—Low.
*Grade of floral abscission.*—Medium.
*Blooming time.*—Early.
*Flowering duration.*—Short; May to June and September to October.

Physiological and ecological characteristics:
*Grade of cold resistance.*—Medium.
*Grade of heat resistance.*—Medium.
*Grade of disease resistance.*—Strong.
*Grade of pest resistance.*—Medium.

This new and distinct variety of fuchsia plant. "SANISTANF", was asexually reproduced by cutting at the aforementioned at the Plant Biotechnology Laboratory of SUNTORY Ltd. and the Plant Research Center of NISHINOMIYA-SHI, and the homogeneity and stability thereof were confirmed.

SUMMARY OF THE VARIETY

The new variety of fuchsia plant has a spreading growth habit with strong bushy, yellow green stems, grayish olive green mature leaf without pubescence and thick stem is very different from a similar variety, "Fuchsia hybrida 1"(♀) having spreading growth habit with medium bushiness, dark yellowish green mature leaf with pubescence and medium stem. The brace roots and stems of the new variety of fuchsia plant are thick and strong, and so it needs no support. The new variety of fuchsia plant has a great profusion blooms and very long flowering duration, deep violet to moderate purple flower petals without variegated pattern, vivid red sepal without variegated pattern and vivid red calyx tube without variegated pattern, which is clearly distinguished from "Fuchsia hybrida 1"(♀) having pinkish white flower petals with purple vein pattern, deep pink sepal with vivid red vein pattern and deep pink calyx tube with vivid red vein pattern. The new variety of fuchsia plant has a high resistance to heat, cold, and disease, and it is able to grow in outdoor gardens during the term of intensity of summer heat.

DESCRIPTION OF THE VARIETY

Figure 1:
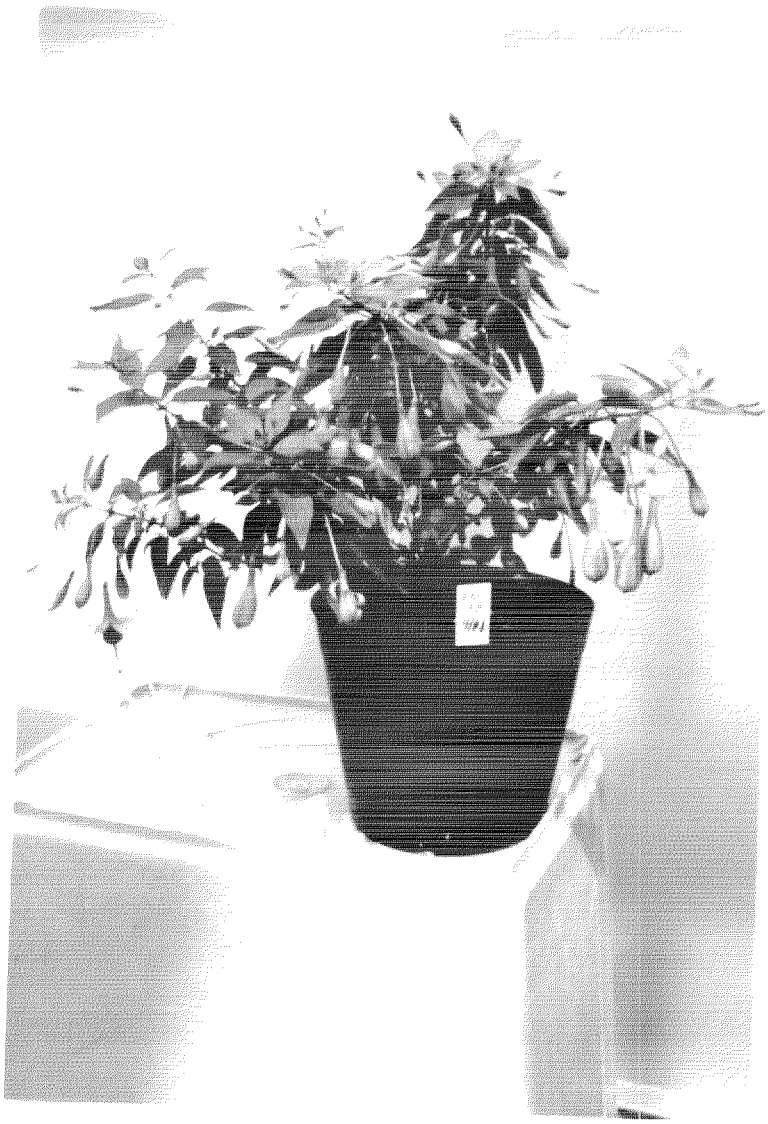
FIG. 1 is a photograph giving a partial view of the new variety of fuchsia plant planted in a flower pot.
Figure 2:
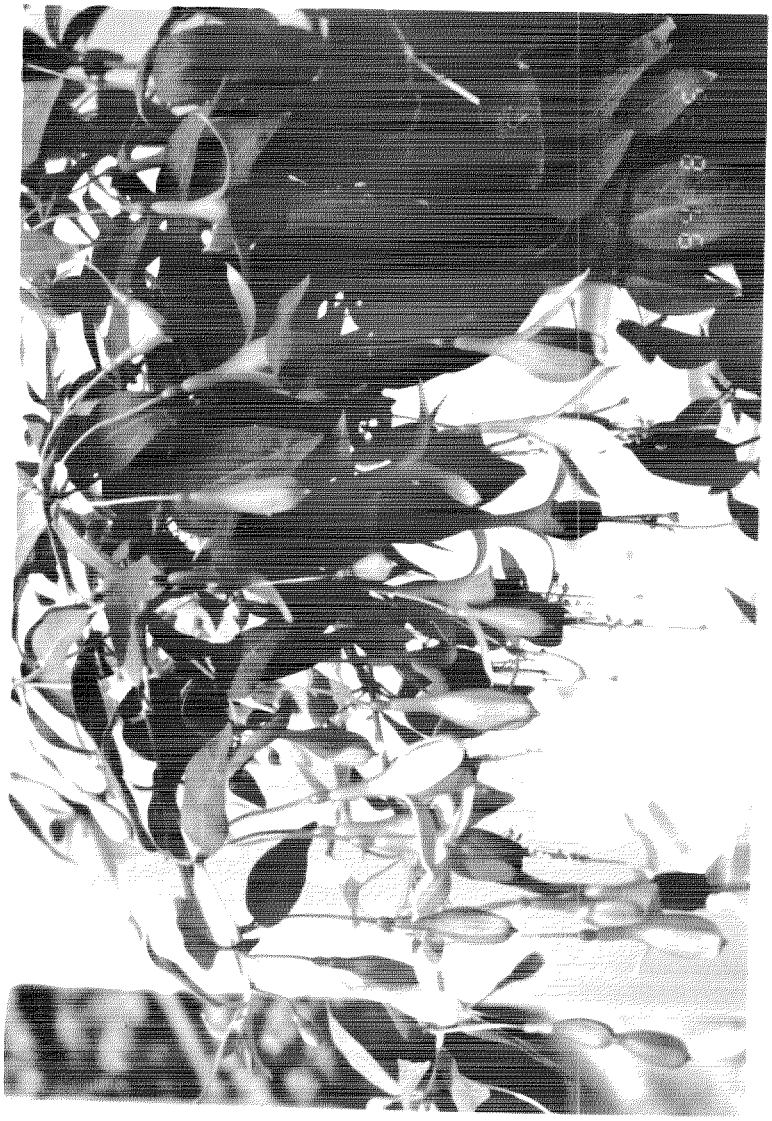
FIG. 2 is a photograph of flowers of the new variety of fuchsia plant.

The botanical characteristics of the new and distinct variety of fuchsia plant "SANISTANF" are as follows.

Plant:
*Growth habit.*—Spreading.
*Plant height.*—Medium.
*Grade of bushiness.*—Many stems.

Stem:
*Thickness.*—2.9 mm.
*Color.*—Yellow green.
*Pubescence.*—Few.
*Branching.*—Medium.
*Length of internode.*—Medium.

Leaf:
*Phyllotaxis.*—Opposite, partially 3-verticillate.
*Shape.*—Ovate.
*Tip form of leaf.*—Acuminate.
*Base form of leaf.*—Orbicular.
*Shape of margin.*—Dentate serrate.
*Length.*—47.9 mm.
*Width.*—28.2 mm.
*Thickness.*—0.4 mm.
*Color of upper surface of new leaf.*—Moderate yellow green. (R.H.S. 146B, J.H.S. 3514).

*Color of upper surface of mature leaf.*—Grayish olive green. (R.H.S. 137A, J.H.S. 3716).
*Color of under surface of mature leaf.*—Moderate yellow green (R.H.S. 146B, J.H.S. 3514) with dark red. (R.H.S. 59A, J.H.S. 0110) dots.
*Variegation on upper surface.*—Absent.
*Color of leaf vein.*—Dark red. (R.H.S. 59A, J.H.S. 0110).
*Luster.*—Absent.
*Pubescence of upper surface.*—Absent.
*Pubescence of under surface.*—Absent.
*Length of petiole.*—12.5 mm.
*Width of petiole.*—1.1 mm.
*Color of petiole.*—Dark red. (R.H.S. 59A, J.H.S. 0110).
*Pubescence of petiole.*—Few.

Flower:
*Inflorescence types.*—Leaf axil — single.
*Facing direction.*—Downward to horizontal.
*Type.*—Single.
*Diameter.*—43.4 mm.
*Length.*—33.1 mm.
*Diameter of corolla.*—Medium.
*Shape of petal.*—Obovate.
*Length of petal.*—16.2 mm.
*Width of petal.*—19.9 mm.
*Thickness of petal.*—0.4 mm.
*Number of petals.*—Medium: 4.
*Color of petal at the beginning of blooming time.*—Deep violet. (R.H.S. 93A, J.H.S. 8006).
*Color of petal at blooming time.*—Moderate purple. (R.H.S. 83B, J.H.S. 8613).
*Variegated pattern of petal.*—Absent.
*Shape of sepal.*—Oblong.
*Tip form of sepal.*—Acute.
*Calyx rolling.*—Medium (half up).
*Intorsion of sepal.*—None.
*Curvature of sepal.*—Outcurve.
*Length of sepal.*—28.8 mm.
*Width of sepal.*—11.0 mm.
*Thickness of sepal.*—0.7 mm.
*Number of sepals.*—Medium; 4.
*Color of sepal.*—Vivid red. (R.H.S. 62A, J.H.S. 0106).
*Variegated pattern on sepal.*—Absent.
*Shape of calyx tube.*—Long-tubular.
*Thickness of calyx tube.*—5.0 mm.
*Length of calyx tube.*—14.3 mm.
*Color of calyx tube.*—Vivid red. (R.H.S. 52A, J.H.S 0106).
*Variegated pattern on calyx tube.*—Absent.
*Length of pistil.*—Long.

*Color of pistil.*—Deep purplish pink. (R.H.S. 55A, J.H.S. 9705).
*Color of stigma.*—Moderate purplish red. (R.H.S. 58A, J.H.S. 9714).
*Length of stamen.*—Long.
*Color of stamen.*—Strong purplish red. (R.H.S. 60D, J.H.S. 9708).
*Number of stamens.*—Medium; 8.
*Thickness of peduncle.*—Medium.
*Length of peduncle.*—Medium.
*Color of peduncle.*—Pale yellowish pink. (R.H.S. 37D, J.H.S. 1002).
*Shape of ovary.*—Oblong.
*Length of ovary.*—Medium.
*Color of ovary.*—Light yellow green. (R.H.S. 144D, J.H.S. 3503).
*Number of flowers.*—Medium.
*Flower fragrance.*—Absent.
*Floriferousness.*—Numerous flowers.
*Grade of seed fertility.*—Medium.
*Grade of floral abscission.*—Medium.
*Blooming time.*—Early.
*Flowering duration.*—Long: early May to the middle of December.

Physiological and ecological characteristics:
*Grade of cold resistance.*—Strong.
*Grade of heat resistance.*—Strong.
*Grade of disease resistance.*—Strong.
*Grade of pest resistance.*—Medium.

This new variety of fuchsia plant is most suitable for flower potting and bedding, particularly in pots and planters.

The plant of this new variety "SANISTANF" is presently planted and maintained at the Plant Biotechnology Laboratory of SUNTORY Ltd., residing at 863-1, Aza-Iketani, Oomori-cho, Youkaichi-shi, Shiga-ken, Japan and at the Plant Research Center of NISHINOMIYA-SHI, residing at 1-1, Kitayama-cho, Nishinomiya-shi, Hyogo-ken, Japan.

We claim:

1. A new and distinct variety of fuchsia plant, substantially as herein illustrated and described, characterized particularly as to novelty by (A) being a spreading growth habit plant with strong bushy and thick stem, (B) great profusion blooms, the whole bush remaining in bloom for a considerable period of time, and very long flowering duration, (C) having flowers which are single without variegated pattern on petals which is deep violet to moderate purple color, (D) having vivid red sepals without variegated pattern and vivid red calyx without variegated pattern, and (E) a high resistance to heat, cold, and disease.

* * * * *

1/2